United States Patent [19]

Ohdaira et al.

[11] Patent Number: 5,132,243

[45] Date of Patent: Jul. 21, 1992

[54] CARRIER LATEX FOR USE AS DIAGNOSTIC REAGENT

[75] Inventors: Akio Ohdaira; Hiroshi Nishikawa, both of Yamaguchi, Japan

[73] Assignee: Mitsui Petrochemical Industries, Ltd., Tokyo, Japan

[21] Appl. No.: 183,734

[22] PCT Filed: Sep. 9, 1987

[86] PCT No.: PCT/JP87/00667

§ 371 Date: Mar. 9, 1988

§ 102(e) Date: Mar. 9, 1988

[87] PCT Pub. No.: WO88/02119

PCT Pub. Date: Mar. 24, 1988

[30] Foreign Application Priority Data

Sep. 9, 1986 [JP]  Japan ............................. 61-210547

[51] Int. Cl.$^5$ .......................................... G01N 33/546
[52] U.S. Cl. .................................... 436/533; 436/805; 524/460
[58] Field of Search ............... 436/518, 533, 534, 531; 524/460

[56] References Cited

FOREIGN PATENT DOCUMENTS 0008682 3/1980 European Pat. Off. .
61-266420 11/1986 Japan .

OTHER PUBLICATIONS

Chemical Abstracts, vol. 98, 1983, p. 352, abstract No. 50013a, Columbus, Ohio, US.

*Primary Examiner*—Glennon H. Hollrah
*Assistant Examiner*—Brian M. Burn
*Attorney, Agent, or Firm*—Birch, Stewart, Kolasch & Birch

[57] ABSTRACT

A carrier latex for use as a diagnostic reagent, comprising a suspension of particles of a copolymer of ethylene and an α,β-ethylenically unsaturated carboxylic acid, a salt of an α,β-ethylenically unsaturated carboxylic acid or a mixture thereof, having an aromatic vinyl compound grafted thereto, the particles possessing a carboxyl group on the surface thereof, can be used in immuno-serological diagnosis utilizing antigen-antibody reaction, while markedly reducing nonspecific agglutination which undesirably occurs in the prior art and increasing the sensitivity of specific agglutination, and is best suited for application to an immuno-serological diagnosis system relying on an optical measurement.

10 Claims, 1 Drawing Sheet

F I G. 1
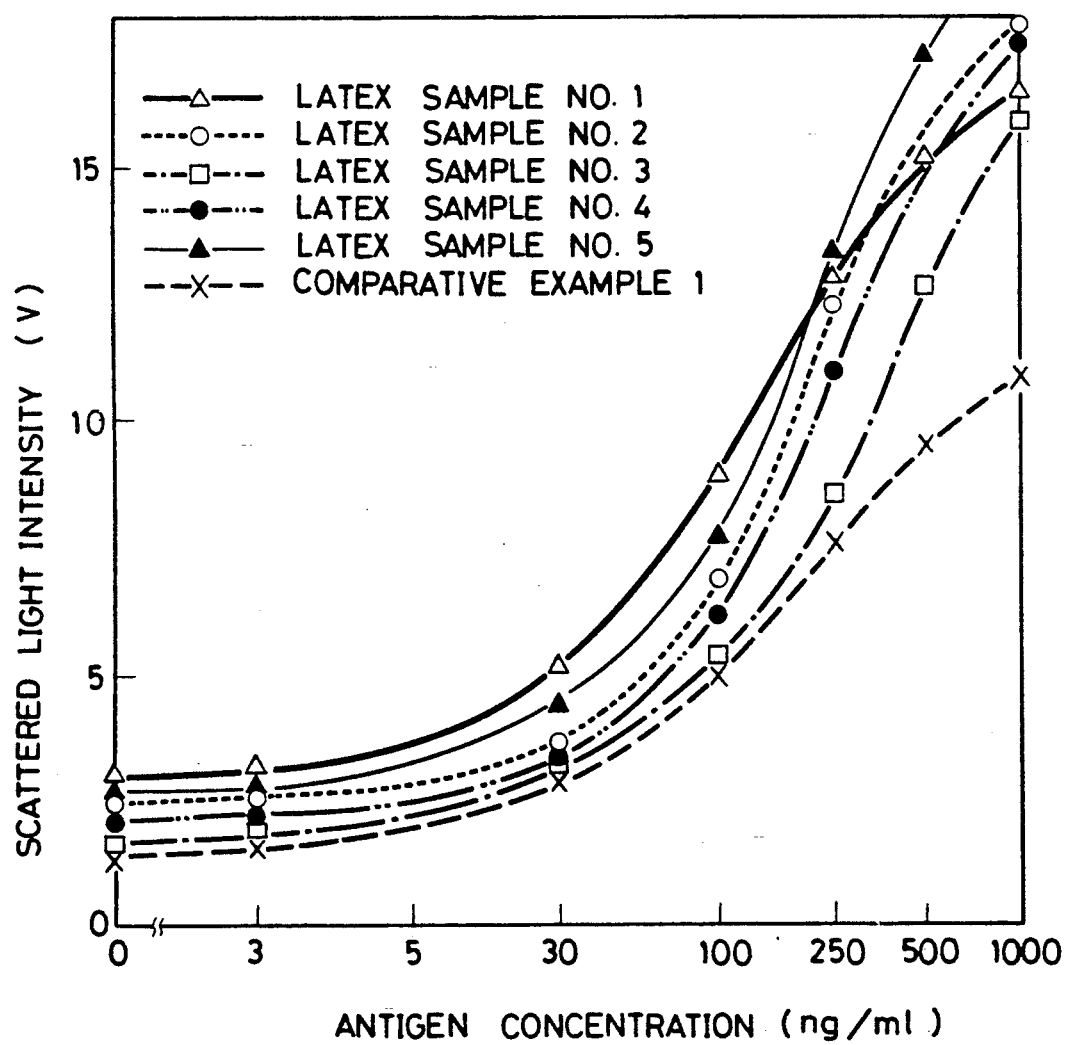

CARRIER LATEX FOR USE AS DIAGNOSTIC REAGENT

FIELD OF THE INVENTION

The present invention relates to a carrier latex for use as a diagnostic reagent which can be used in immunoserological diagnosis utilizing an antigen-antibody reaction while minimizing nonspecific agglutination.

BACKGROUND OF THE INVENTION

Immuno-serological diagnosis is carried out by sensitizing a carrier latex with a serologically active material such as an antigen or antibody, combining the serum to be tested with the latex, and allowing agglutination to take place in the latex, resulting in the detection of the presence of the corresponding antibody or antigen in the serum. Because of its ease and quickness, the immuno-serological diagnosis is widely applied to reagents in the clinical examination art in order to detect a variety of antigens or antibodies.

For this type of diagnostic reagent, carriers to be sensitized with an antigen or antibody are generally formed of resin latices, for example, latices of polystyrene and styrene-butadiene copolymers. These resin latices are required to form a stable emulsion, not to agglutinate during sensitization with an antigen or antibody, and not to agglutinate upon contact with a negative serum when the latices are observed for agglutination by reacting with an antibody or antigen which corresponds to the sensitizing antigen or antibody, that is, to be free of nonspecific agglutination.

Presently, not only qualitative, but also quantitative determination of trace amounts of a material such as antigen or antibody are crucial in the field of immuno-serological diagnostic examination. A prior art practice is the qualitative detection of a subject material being tested which is carried out by mixing and reacting a sensitized latex with the subject material to be tested on a glass plate and visually observing the agglutination of the particles in the latex. Numerous attempts have been made to achieve quantitative detection by a measurement using an optical instrument such as a spectrophotometer, turbidimeter, and quasi-elastic scattered light meter instead of the visual observation of agglutination. A method of detecting a reduction in tubidity of supernatant by utilizing the phenomenon that particles agglutinate in the sensitized latex, and a method of measuring a variation of absorbance or scattered light due to agglutination of particles in the sensitized latex, are known. See CROATICA CHEMICA ACTA, 42. 457 (1970), Immunochemistry, 12, 349 (1975), and Japanese Patent Application Kokai Nos. 53-24015 and 54-109494.

These methods achieve quantitative measurement by determining the variation of the optical properties, such as absorbance and scattered light intensity, of a reaction system due to the immuno-serological agglutination of particles in a sensitized latex. However, these methods are not sufficiently accurate and are not capable of consistent reproduction because only a small variation occurs in the optical properties of a reaction system due to the agglutination. Further, quite often the optical properties of a sensitized latex will change with time, which creates a problem for obtaining a practical measurement.

A latex may be sensitized with an antigen or antibody either by physical adsorption or by chemical bonding. Because an adsorption-dissociation equilibrium does exist between the latex and the antigen or antibody with which the latex is sensitized, a commonly used sensitization method based on physical adsorption would have the drawback that there is the possibility of the antigen or antibody dissociating from the latex during measurement or storage.

It is, therefore, an object of the present invention to provide a carrier latex for use as a diagnostic reagent which is free from the above-mentioned problems of conventional diagnostic reagent carrier latices, and can be used in an immuno-serological diagnostic test utilizing an antigen-antibody reaction while experiencing minimized nonspecific agglutination reaction. Another object is to provide a carrier latex which is suitable for the optical measurement of absorbance and scattered light intensity.

DISCLOSURE OF THE INVENTION

In the course of conducting extensive investigations to attain the above-mentioned objects, the present inventors have discovered that these objects can be attained by providing a latex comprising particles of a copolymer of ethylene and an $\alpha,\beta$-ethylenically unsaturated carboxylic acid, a salt of an $\alpha,\beta$-ethylenically unsaturated carboxylic acid or a mixture thereof, having an aromatic vinyl compound grafted thereto, the particles having a carboxyl group on the surface thereof. The present invention is predicated on this finding.

According to the present invention, there is provided a carrier latex for use as a diagnostic reagent, comprising a suspension of particles of a copolymer of ethylene and an $\alpha,\beta$-ethylenically unsaturated carboxylic acid, a salt of an $\alpha,\beta$-ethylenically unsaturated carboxylic acid or a mixture thereof, having an aromatic vinyl compound grafted thereto, the particles possessing a carboxyl group on the surface thereof.

Preferably, the copolymer of ethylene and an $\alpha,\beta$-ethylenically unsaturated carboxylic acid, a salt of an $\alpha,\beta$-ethylenically unsaturated carboxylic acid or a mixture thereof is a copolymer comprising from 65 to 98% by weight of ethylene and from 2 to 35% by weight of an $\alpha,\beta$-ethylenically unsaturated carboxylic acid, a salt of an $\alpha,\beta$-ethylenically unsaturated carboxylic acid, or a mixture thereof.

The carboxyl group on the surface of the suspended particles may preferably range from 0.01 to 0.3 meq/gram based on the weight of the particles.

The suspended particles may preferably have an average particle size of from 0.05 to 1 $\mu$m and a specific gravity of at least 1.

The latex may preferably have a solid content of from 5 to 45% by weight.

Preferably, the $\alpha,\beta$-ethylenically unsaturated carboxylic acid is at least one carboxylic acid selected from the group consisting of acrylic acid, methacrylic acid, itaconic acid, maleic acid, and fumaric acid and the salt of the $\alpha,\beta$-ethylenically unsaturated carboxylic acid is at least one metal salt selected from the group consisting of a sodium salt, a potassium salt, a magnesium salt, a calcium salt, a barium salt, and a zinc salt of these carboxylic acids.

The aromatic vinyl compound to be grafted is at least one member selected from the group consisting of styrene, $\alpha$-methylstyrene, vinyltoluene, and ethylstyrene, and is grafted in a proportion of from 100 to 900 parts by weight per 100 parts by weight of the copolymer of ethylene and an α,β-ethylenically unsaturated carboxylic acid, a salt of an α,β-ethylenically unsaturated carboxylic acid or a mixture thereof, and the copolymer to which the aromatic vinyl compound is to be grafted has a melt flow rate of 50 to 700 gram/10 min. as measured at 190° C. under a load of 2.16 kg.

BRIEF DESCRIPTION OF THE DRAWING

FIG. 1 illustrates the scattered light intensity associated with the agglutination reaction of the carrier latices which are prepared in Example 1 as sample Nos. 1 to 5 and Comparative Example 1 and are sensitized with an anti-AFP antibody, as a function of antigen concentration.

DETAILED DESCRIPTION OF THE INVENTION

The carrier latex for use as a diagnostic reagent of the present invention will be described in further detail.

The carrier latex for use as a diagnostic reagent according to the present invention is a suspension of particles of a copolymer of ethylene and an α,β-ethylenically unsaturated carboxylic acid, a salt of an α,β-ethylenically unsaturated carboxylic acid or a mixture thereof, having an aromatic vinyl compound grafted thereto, the particles bearing a carboxyl group attached to the surface thereof. More particularly, the latex may be obtained by grafting an aromatic vinyl compound to suspended particles of a copolymer of ethylene and an α,β-ethylenically unsaturated carboxylic acid, a salt of an α,β-ethylenically unsaturated carboxylic acid or a mixture thereof.

The copolymer of ethylene and an α,β-ethylenically unsaturated carboxylic acid, a salt of an α,β-ethylenically unsaturated carboxylic acid or a mixture thereof used herein is generally a copolymer comprising from 65 to 98% by weight, preferably from 80 to 98% by weight of ethylene and from 2 to 35% by weight, preferably from 2 to 20% by weight of an α,β-ethylenically unsaturated carboxylic acid or carboxylate.

The α,β-ethylenically unsaturated carboxylic acids or carboxylates encompass α,β-ethylenically unsaturated carboxylic acids or their salts, or mixtures thereof. Their examples include such α,β-ethylenically unsaturated carboxylic acids as acrylic, methacrylic, itaconic, maleic, and fumaric acid, and metal salts thereof such as sodium, potassium, magnesium, calcium, barium, and zinc salts of these carboxylic acids. Of these acids and salts, methacrylic acid and its salts are preferred. The copolymers may also be fully or partially neutralized products of the copolymer of ethylene and an α,β-ethylenically unsaturated carboxylic acid, a salt of an α,β-ethylenically unsaturated carboxylic acid or a mixture thereof.

Prior to grafting of an aromatic vinyl compound, the copolymers generally have a melt flow rate of from 50 to 700 gram/10 min., preferably from 100 to 600 gram/10 min. as measured at 190° C. under a load of 2.16 kg.

In the suspension of the copolymer of ethylene and an α,β-ethylenically unsaturated carboxylic acid, a salt of an α,β-ethylenically unsaturated carboxylic acid or a mixture thereof prior to grafting of an aromatic vinyl compound thereto, the copolymer particles generally have an average particle size of from 0.03 to 1 μm, preferably from 0.04 to 0.8 μm.

The proportion of an aromatic vinyl compound grafted to the copolymer of ethylene and an α,β-ethylenically unsaturated carboxylic acid, a salt of an α,β-ethylenically unsaturated carboxylic acid or a mixture thereof to constitute suspended particles of the carrier latex for use as a diagnostic reagent according to the present invention, generally ranges from 100 to 900 parts by weight, preferably from 200 to 800 parts by weight per 100 parts by weight of the copolymer. Examples of the aromatic vinyl compound include styrene, α-methylstyrene, vinyltoluene, ethylstyrene, and the like.

In the carrier latex for use as a diagnostic reagent, the suspended particles generally have an average particle size of from 0.05 to 1 μm, preferably from 0.1 to 0.3 μm, with a narrower particle size distribution being preferred. The carrier latex for use as a diagnostic reagent generally has a solid content of from 5 to 45% by weight, preferably from 10 to 35% by weight.

Since the carrier latex is often subjected to centrifugal separation in a subsequent sensitizing step or sensitized latex separating step, the suspended particles in the carrier latex may generally have a specific gravity of at least 1, preferably from 1.0 to 1.1.

The suspended particles of the carrier latex for use as a diagnostic reagent of the present invention have attached on the surface a carboxyl group capable of chemically bonding an immuno-serologically active material such as an antigen or antibody. The amount of carboxyl group present on the particle surface generally ranges from 0.01 to 0.3 meq/gram based on the weight of the particles, preferably from 0.02 to 0.1 meq/gram based on the weight of the particles. The latex tends to give rise to nonspecific agglutination with a lesser carboxyl group content whereas the latex tends to reduce its agglutination reactivity and hence, its sensitivity with a larger carboxyl group content. The amount of carboxyl group present on the surface of suspended particles of the carrier latex may be determined by the measurement method developed by Johnhen. See Journal of Colloid and Interface Science, 49, 425 (1974).

The preparation of the carrier latex for use as a diagnostic reagent according to the present invention will be described.

The carrier latex may be prepared, for example, by combining a suspension of a copolymer of ethylene and an α,β-ethylenically unsaturated carboxylic acid, a salt of an α,β-ethylenically unsaturated carboxylic acid or a mixture thereof, an aromatic vinyl compound in an amount of 100 to 900 parts per 100 parts by weight of the solids of the suspension, and water at a temperature of from 50 to 100° C., adding an aqueous persulfate solution to the mixture, and allowing graft polymerization to proceed for 1 to 6 hours. The persulfates include ammonium persulfate, sodium persulfate, and potassium persulfate, and may be used in an amount of 0.1 to 5% by weight based on the weight of the aromatic vinyl compound. The polymerization temperature preferably ranges from 50 to 100° C., more preferably from 70 to 90° C. At the end of the polymerization, vacuum distillation may be carried out to remove the unreacted monomer and/or the product may be diluted or concentrated to control the concentration.

The carrier latex for use as a diagnostic reagent of the present invention may be sensitized or chemically bonded with an immuno-serologically active material such as an antigen or antibody by any known prior art method.

BEST MODE FOR CARRYING OUT THE INVENTION

Examples of the present invention are given below by way of illustration and not by way of limitation. The following methods were employed to carry out sensitization of a latex with an antibody and measurement of the agglutination sensitivity of the sensitized latex.

(1) Latex sensitization

Preparation of anti-AFP latex reagent

A resin latex is suspended in a phosphate buffer solution to obtain 0.25 ml of a suspension having a solid concentration of 5%. To the suspension are added 1 mg of an IgG fraction prepared from anti-AFP (alpha-fetoprotein) rabbit serum and 5 mg of water-soluble carbodiimide. The mixture is adjusted to pH 5 and stirred for one hour under ice cooling to chemically bond IgG to the latex surface. Then the reaction mixture is combined with glycine, adjusted to pH 8, centrifuged at 20,000 rpm for 30 minutes, removed of the supernatant, and dispersed again in a glycine buffer solution (pH 8.2) containing 3% by weight of human serum albumin, obtaining a sensitized latex having a solid concentration of 0.1%.

(2) Measurement of agglutination sensitivity

The sensitized latex, 50 μl is diluted with 150 μl of a glycine buffer solution (pH 8.2) containing 1% by weight of bovine serum albumin, combined with 10 μl of a sample containing a predetermined concentration of AFP, stirred for mixing, and allowed to react for 30 minutes at room temperature. The scattered light intensity of the mixture is measured by a scattered light measuring intensity to AFP concentration.

EXAMPLE 1

Preparation of ionomer dispersion

A solution was prepared by heating 100 grams of an ethylene-methacrylic acid copolymer containing 10% by weight of methacrylic acid in 330 grams of toluene and 220 grams of isopropyl alcohol to 75° C. The solution was added to 250 grams of distilled water containing 0.78 grams of sodium hydroxide in a homomixer and agitated for 10 to 20 minutes. The toluene and isopropyl alcohol were concentration to 30%. Dispersions having different particle sizes were obtained by varying the polymer concentration of the oily layer and the weight ratio of toluene to isopropyl alcohol as shown in Table 1.

TABLE 1

| | Sample | | |
|---|---|---|---|
| | A | B | C |
| Composition of oily layer | | | |
| Ethylene-methacrylic acid copolymer (gram) | 100 | 80 | 100 |
| Toluene (gram) | 330 | 330 | 385 |
| Isopropyl alcohol (gram) | 220 | 220 | 165 |
| Composition of aqueous layer | | | |
| Sodium hydroxide (gram) | 0.78 | 0.62 | 0.78 |
| Distilled water (gram) | 250 | 250 | 250 |
| Average particle size (μm) | 0.16 | 0.10 | 0.24 |

Styrene graft polymerization of ionomer dispersion

A mixture of the above-prepared ionomer dispersion, styrene, and distilled water in the proportion shown in Table 2 was heated at 80° C., combined with 50 grams of distilled water containing potassium persulfate, and stirred for 2 hours at 80° C. for polymerization. The resulting polymer particle latex was subjected to vacuum distillation to remove the unreacted styrene. The average particle size and surface carboxyl group content of the polymer particles are also shown in Table 2.

TABLE 2

| | Sample Nos. of Example 1 | | | | |
|---|---|---|---|---|---|
| | 1 | 2 | 3 | 4 | 5 |
| Ionomer dispersion (type) | A | A | A | B | C |
| (gram) | 67 | 100 | 133 | 100 | 100 |
| Styrene (gram) | 80 | 70 | 60 | 70 | 70 |
| Distilled water (gram) | 103 | 80 | 57 | 80 | 80 |
| Potassium persulfate (gram) | 0.4 | 0.35 | 0.3 | 0.35 | 0.35 |
| Average particle size (μm) | 0.19 | 0.18 | 0.17 | 0.12 | 0.26 |
| Surface carboxyl group content (meq/g) | 0.04 | 0.06 | 0.08 | 0.07 | 0.05 |

Comparative Example 1

Preparation of styrene-methacrylic acid copolymer particle latex

Distilled water, 150 grams, was heated to 80° C. with stirring. Then a mixture of 98 grams of styrene and 2 grams of methacrylic acid and 50 grams of distilled water containing 0.5 grams of potassium persulfate were simultaneously and continuously added to the water over a period of 10 hours. At the end of addition, the mixture was stirred for a further 2 hours to complete polymerization. The resulting polymer particle latex was subjected to vacuum distillation to remove the unreacted monomers. The resulting polymer particles had an average particle size of 0.20 μm and a surface carboxyl group content of 0.06 meq/g.

The carrier latices prepared in Example 1 and Comparative Example 1 were sensitized with an anti-AFP antibody according to the above-described latex sensitizing procedure (1) to produce sensitized latices, which were measured for agglutination sensitivity according to the above-described agglutination sensitivity measuring procedure (2). The results are shown in FIG. 1.

As evident from FIG. 1, the sensitized latices using latex sample Nos. 1 to 5 of Example 1 exhibit a marked change in scattered light intensity with the AFP concentration. In contrast, the sensitized latex using the latex of Comparative Example 1 exhibits a less change in scattered light intensity with the AFP concentration.

INDUSTRIAL APPLICABILITY

A carrier latex ready for use as diagnostic reagent which is prepared from a diagnostic reagent carrier latex according to the present invention, that is, sensitized latex exhibits minimized nonspecific agglutination and high sensitivity to specific agglutination, and is thus optimum for use in a diagnostic system based on optical measurement.

We claim:

1. A carrier latex for use as a diagnostic reagent, comprising a suspension of particles of a copolymer of
   ethylene and
   an α, β-ethylenically unsaturated carboxylic acid containing 3 to 5 carbon atoms or a salt of an α,β-ethylenically unsaturated carboxylic acid containing 3 to 5 carbon atoms, or a mixture of an α, β-ethylenically unsaturated carboxylic acid containing 3 to 5 carbon atoms and a salt of an α,β-ethylenically unsaturated carboxylic acid containing 3 to 5 carbon atoms,
   having an aromatic vinyl compound containing a phenyl group a methylphenyl group or an ethylphenyl group grafted thereto,
   wherein the proportion of the aromatic vinyl compound grafted ranges from 100 to 900 parts by weight per 100 parts by weight of the copolymer, said particles having a carboxylic group on the surface thereof.

2. The carrier latex for use as a diagnostic reagent according to claim 1 wherein said copolymer comprises from 65 to 98% by weight of ethylene and from 2 to 35% by weight of an α,β-ethylenically unsaturated carboxylic acid containing 3 to 5 carbon atoms or a salt of an α,β-ethylenically unsaturated carboxylic acid containing 3 to 5 carbon atoms, or a mixture of an α,β-ethylenically unsaturated carboxylic acid containing 3 to 5 carbon atoms and a salt of an α,β-ethylenically unsaturated carboxylic acid containing 3 to 5 carbon atoms.

3. The carrier latex for use as a diagnostic reagent according to claim 1 wherein the carboxyl group on the surface of said suspended particles ranges from 0.01 to 0.3 meq/gram based on the weight of the particles.

4. The carrier latex for use as a diagnostic reagent according to claim 1 wherein said suspended particles have an average particle size of from 0.05 to 1 μm.

5. The carrier latex for use as a diagnostic reagent according to claim 1 wherein said latex has a solid content of from 5 to 45% by weight.

6. The carrier latex for use as a diagnostic reagent according to claim 5 wherein the particles suspended in said latex have a specific gravity of at least 1.

7. The carrier latex for use as a diagnostic reagent according to claim 2 wherein said α,β-ethylenically unsaturated carboxylic acid is at least one carboxylic acid selected from the group consisting of acrylic acid, methacrylic acid, itaconic acid, maleic acid, and fumaric acid and said salt of an α,β-ethylenically unsaturated carboxylic acid is at least one metal salt selected from the group consisting of a sodium salt, a potassium salt, a magnesium salt, a calcium salt, a barium salt, and a zinc salt.

8. The carrier latex for use as a diagnostic reagent according to claim 1 wherein said copolymer, prior to grafting of the aromatic vinyl compound, has a melt flow rate of 50 to 700 gram/10 min. as measured at 190° C. under a load of 2.16 kg.

9. The carrier latex for use as a diagnostic reagent according to claim 1 wherein the phenyl-, methylphenyl- or ethylphenyl group-containing aromatic vinyl compound grafted is at least one member selected from the group consisting a styrene, α-methylstyrene, vinyltoluene and ethylstyrene.

10. The carrier latex for use as a diagnostic reagent according to claim 9 wherein the proportion of the aromatic vinyl grafted ranges from 200 to 800 parts by weight per 100 parts by weight of said copolymer.

* * * * *